US008231620B2

(12) United States Patent (10) Patent No.: US 8,231,620 B2
Mathonnet (45) Date of Patent: Jul. 31, 2012

(54) EXTENSION CUTTING BLADE (75) Inventor: Olivier Mathonnet, Chassieu (FR)

(73) Assignee: TYCO Healthcare Group LP, Mansfield, MA (US)

( * ) Notice: Subject to any disclaimer, the term of this patent is extended or adjusted under 35 U.S.C. 154(b) by 629 days.

(21) Appl. No.: 12/368,463

(22) Filed: Feb. 10, 2009

(65) Prior Publication Data
US 2010/0204696 A1 Aug. 12, 2010

(51) Int. Cl.
*A61B 18/18* (2006.01)
(52) U.S. Cl. ........................................................ 606/47
(58) Field of Classification Search .................... 606/45, 606/47
See application file for complete search history.

(56) References Cited

U.S. PATENT DOCUMENTS

| | | | |
|---|---|---|---|
| 2,031,682 A | 2/1936 | Charles et al. | |
| 2,102,270 A | 12/1937 | Hyams | |
| 2,964,796 A | 12/1960 | Press | |
| 2,993,178 A | 7/1961 | Burger | |
| 3,058,470 A | 10/1962 | Seeliger et al. | |
| 3,219,029 A | 11/1965 | Richards et al. | |
| 3,460,539 A | 8/1969 | Anhalt, Sr. | |
| 3,494,363 A | 2/1970 | Jackson | |
| 3,648,001 A | 3/1972 | Anderson et al. | |
| 3,675,655 A | 7/1972 | Sittner | |
| 3,699,967 A | 10/1972 | Anderson | |
| 3,720,896 A | 3/1973 | Beierlein | |
| 3,801,766 A | 4/1974 | Morrison, Jr. | |
| 3,801,800 A | 4/1974 | Newton | |
| 3,825,004 A * | 7/1974 | Durden, III | 604/20 |
| 3,828,780 A | 8/1974 | Morrison, Jr. | |
| 3,875,945 A * | 4/1975 | Friedman | 606/45 |
| 3,902,494 A | 9/1975 | Haberlen et al. | |
| 3,906,955 A | 9/1975 | Roberts | |
| 3,911,241 A | 10/1975 | Jarrard | |
| 3,967,084 A | 6/1976 | Pounds | |
| 3,974,833 A * | 8/1976 | Durden, III | 604/20 |
| 4,014,343 A | 3/1977 | Esty | |
| 4,032,738 A | 6/1977 | Esty et al. | |
| 4,034,761 A | 7/1977 | Prater et al. | |
| 4,038,984 A | 8/1977 | Sittner | |
| 4,043,342 A * | 8/1977 | Morrison, Jr. | 606/48 |
| 4,112,950 A | 9/1978 | Pike | |
| D253,247 S | 10/1979 | Gill | |
| 4,232,676 A | 11/1980 | Herczog | |
| 4,314,559 A | 2/1982 | Allen | |
| 4,427,006 A | 1/1984 | Nottke | |
| 4,443,935 A | 4/1984 | Zamba et al. | |
| 4,459,443 A | 7/1984 | Lewandowski | |
| 4,463,234 A | 7/1984 | Bennewitz | |
| 4,463,759 A | 8/1984 | Garito et al. | |

(Continued)

FOREIGN PATENT DOCUMENTS

DE 24 29 021 A1 1/1976

(Continued)

OTHER PUBLICATIONS

International Search Report EP10153021 dated Nov. 12, 2010.

(Continued)

*Primary Examiner* — Christopher D Koharski
*Assistant Examiner* — Diva K Chander (57) ABSTRACT

The present disclosure relates to an apparatus, a system, and a method of electrosurgery to maximize the manipulability of instrumentation inserted at a single access point.

21 Claims, 4 Drawing Sheets

U.S. PATENT DOCUMENTS

| | | | |
|---|---|---|---|
| 4,492,231 A | 1/1985 | Auth | |
| 4,492,832 A | 1/1985 | Taylor | |
| 4,545,375 A | 10/1985 | Cline | |
| 4,562,838 A | 1/1986 | Walker | |
| 4,589,411 A | 5/1986 | Friedman | |
| 4,593,691 A | 6/1986 | Lindstrom et al. | |
| 4,595,809 A | 6/1986 | Pool | |
| 4,606,342 A | 8/1986 | Zamba et al. | |
| 4,619,258 A | 10/1986 | Pool | |
| 4,620,548 A | 11/1986 | Hasselbrack | |
| 4,625,723 A | 12/1986 | Altnether et al. | |
| 4,640,279 A | 2/1987 | Beard | |
| 4,642,128 A | 2/1987 | Solorzano | |
| 4,655,215 A | 4/1987 | Pike | |
| 4,657,016 A | 4/1987 | Garito et al. | |
| 4,683,884 A | 8/1987 | Hatfield et al. | |
| 4,688,569 A | 8/1987 | Rabinowitz | |
| 4,701,193 A | 10/1987 | Robertson et al. | |
| 4,712,544 A | 12/1987 | Ensslin | |
| 4,735,603 A | 4/1988 | Goodson et al. | |
| 4,754,754 A | 7/1988 | Garito et al. | |
| 4,785,807 A | 11/1988 | Blanch | |
| 4,788,977 A | 12/1988 | Farin et al. | |
| 4,794,215 A | 12/1988 | Sawada et al. | |
| 4,796,623 A | 1/1989 | Krasner et al. | |
| 4,803,323 A | 2/1989 | Bauer et al. | |
| 4,811,733 A | 3/1989 | Borsanyi et al. | |
| 4,827,911 A | 5/1989 | Broadwin et al. | |
| 4,827,927 A | 5/1989 | Newton | |
| D301,739 S | 6/1989 | Turner et al. | |
| 4,846,790 A | 7/1989 | Hornlein et al. | |
| 4,850,353 A | 7/1989 | Stasz et al. | |
| 4,860,745 A | 8/1989 | Farin et al. | |
| 4,862,889 A | 9/1989 | Feucht | |
| 4,862,890 A | 9/1989 | Stasz et al. | |
| 4,869,715 A | 9/1989 | Sherburne | |
| 4,872,454 A | 10/1989 | DeOliveira et al. | |
| 4,876,110 A | 10/1989 | Blanch | |
| 4,886,060 A | 12/1989 | Wiksell | |
| 4,901,719 A | 2/1990 | Trenconsky et al. | |
| 4,903,696 A | 2/1990 | Stasz et al. | |
| 4,909,249 A | 3/1990 | Akkas et al. | |
| 4,911,159 A | 3/1990 | Johnson et al. | |
| 4,916,275 A | 4/1990 | Almond | |
| 4,919,129 A | 4/1990 | Weber, Jr. et al. | |
| 4,921,476 A | 5/1990 | Wuchinich | |
| 4,922,903 A | 5/1990 | Welch et al. | |
| 4,931,047 A | 6/1990 | Broadwin et al. | |
| 4,949,734 A | 8/1990 | Bernstein | |
| 4,969,885 A | 11/1990 | Farin | |
| 4,986,839 A | 1/1991 | Wertz et al. | |
| 4,988,334 A | 1/1991 | Hornlein et al. | |
| 5,000,754 A | 3/1991 | DeOliveira et al. | |
| 5,011,483 A | 4/1991 | Sleister | |
| 5,013,312 A | 5/1991 | Parins et al. | |
| 5,015,227 A | 5/1991 | Broadwin et al. | |
| 5,026,368 A | 6/1991 | Adair | |
| 5,035,695 A | 7/1991 | Weber, Jr. et al. | |
| 5,035,696 A | 7/1991 | Rydell | |
| 5,046,506 A | 9/1991 | Singer | |
| 5,055,100 A | 10/1991 | Olsen | |
| 5,071,418 A | 12/1991 | Rosenbaum | |
| 5,074,863 A | 12/1991 | Dines | |
| 5,076,276 A | 12/1991 | Sakurai et al. | |
| 5,088,997 A | 2/1992 | Delahuerga et al. | |
| 5,098,430 A | 3/1992 | Fleenor | |
| 5,100,402 A | 3/1992 | Fan | |
| 5,108,391 A | 4/1992 | Flachenecker et al. | |
| 5,133,714 A | 7/1992 | Beane | |
| 5,147,292 A | 9/1992 | Kullas et al. | |
| D330,253 S | 10/1992 | Burek | |
| 5,154,709 A | 10/1992 | Johnson | |
| 5,160,334 A | 11/1992 | Billings et al. | |
| 5,162,044 A | 11/1992 | Gahn et al. | |
| 5,167,659 A | 12/1992 | Ohtomo et al. | |
| 5,178,012 A | 1/1993 | Culp | |
| 5,178,605 A | 1/1993 | Imonti | |
| 5,190,517 A | 3/1993 | Zieve et al. | |
| 5,192,267 A | 3/1993 | Shapira et al. | |
| 5,195,959 A | 3/1993 | Smith | |
| 5,196,007 A | 3/1993 | Ellman et al. | |
| 5,197,962 A | 3/1993 | Sansom et al. | |
| 5,199,944 A | 4/1993 | Cosmescu | |
| 5,217,457 A | 6/1993 | Delahuerga et al. | |
| 5,224,944 A | 7/1993 | Elliott | |
| 5,226,904 A | 7/1993 | Gentelia et al. | |
| 5,233,515 A | 8/1993 | Cosman | |
| 5,234,428 A | 8/1993 | Kaufman | |
| 5,234,429 A | 8/1993 | Goldhaber | |
| 5,242,442 A | 9/1993 | Hirschfeld | |
| 5,244,462 A | 9/1993 | Delahuerga et al. | |
| 5,246,440 A | 9/1993 | Van Noord | |
| 5,254,082 A | 10/1993 | Takase | |
| 5,254,117 A | 10/1993 | Rigby et al. | |
| 5,256,138 A | 10/1993 | Burek et al. | |
| 5,261,906 A | 11/1993 | Pennino et al. | |
| 5,269,781 A | 12/1993 | Hewell, III | |
| 5,300,087 A | 4/1994 | Knoepfler | |
| 5,304,763 A | 4/1994 | Ellman et al. | |
| 5,306,238 A | 4/1994 | Fleenor | |
| 5,312,327 A * | 5/1994 | Bales et al. ................... 604/21 |
| 5,312,329 A | 5/1994 | Beaty et al. | |
| 5,312,400 A | 5/1994 | Bales et al. | |
| 5,312,401 A | 5/1994 | Newton et al. | |
| 5,318,516 A | 6/1994 | Cosmescu | |
| 5,318,565 A | 6/1994 | Kuriloff et al. | |
| 5,322,503 A | 6/1994 | Desai | |
| 5,330,470 A | 7/1994 | Hagen | |
| 5,334,183 A | 8/1994 | Wuchinich | |
| 5,342,356 A | 8/1994 | Ellman et al. | |
| 5,348,555 A | 9/1994 | Zinnanti | |
| 5,366,464 A | 11/1994 | Belknap | |
| 5,376,089 A | 12/1994 | Smith | |
| 5,380,320 A | 1/1995 | Morris | |
| 5,382,247 A | 1/1995 | Cimino et al. | |
| 5,395,363 A | 3/1995 | Billings et al. | |
| 5,399,823 A | 3/1995 | McCusker | |
| 5,401,273 A | 3/1995 | Shippert | |
| 5,403,882 A | 4/1995 | Huggins | |
| 5,406,945 A | 4/1995 | Riazzi et al. | |
| 5,409,484 A | 4/1995 | Erlich et al. | |
| 5,413,575 A | 5/1995 | Haenggi | |
| 5,421,829 A | 6/1995 | Olichney et al. | |
| 5,423,838 A | 6/1995 | Willard | |
| 5,431,645 A | 7/1995 | Smith et al. | |
| 5,431,650 A | 7/1995 | Cosmescu | |
| 5,451,222 A | 9/1995 | De Maagd et al. | |
| 5,460,602 A | 10/1995 | Shapira | |
| 5,462,522 A | 10/1995 | Sakurai et al. | |
| 5,468,240 A | 11/1995 | Gentelia et al. | |
| 5,472,442 A | 12/1995 | Klicek | |
| 5,472,443 A | 12/1995 | Cordis et al. | |
| 5,484,398 A | 1/1996 | Stoddard | |
| 5,484,434 A | 1/1996 | Cartmell et al. | |
| 5,486,162 A | 1/1996 | Brumbach | |
| 5,496,314 A | 3/1996 | Eggers | |
| 5,498,654 A | 3/1996 | Shimasaki et al. | |
| 5,504,687 A * | 4/1996 | Wolf ............................... 700/95 |
| D370,731 S | 6/1996 | Corace et al. | |
| 5,531,722 A | 7/1996 | Van Hale | |
| 5,549,604 A | 8/1996 | Sutcu et al. | |
| 5,561,278 A | 10/1996 | Rutten | |
| 5,601,224 A | 2/1997 | Bishop et al. | |
| 5,609,573 A | 3/1997 | Sandock | |
| 5,626,575 A | 5/1997 | Crenner | |
| 5,630,417 A | 5/1997 | Petersen et al. | |
| 5,630,426 A | 5/1997 | Eggers et al. | |
| 5,630,812 A | 5/1997 | Ellman et al. | |
| 5,633,578 A | 5/1997 | Eggers et al. | |
| 5,634,912 A | 6/1997 | Injev | |
| 5,634,935 A | 6/1997 | Taheri | |
| 5,643,256 A | 7/1997 | Urueta | |
| D384,148 S | 9/1997 | Monson | |
| 5,669,907 A | 9/1997 | Platt, Jr. et al. | |
| 5,673,695 A * | 10/1997 | McGee et al. ................ 600/374 |
| 5,674,219 A | 10/1997 | Monson et al. | |
| 5,693,044 A | 12/1997 | Cosmescu | |

| Patent No. | Date | Name |
|---|---|---|
| 5,693,050 A | 12/1997 | Speiser |
| 5,693,052 A | 12/1997 | Weaver |
| 5,697,926 A | 12/1997 | Weaver |
| 5,702,360 A | 12/1997 | Dieras et al. |
| 5,702,387 A | 12/1997 | Arts et al. |
| 5,712,543 A | 1/1998 | Sjostrom |
| 5,713,895 A | 2/1998 | Lontine et al. |
| 5,720,745 A | 2/1998 | Farin et al. |
| D393,067 S | 3/1998 | Geary et al. |
| 5,749,869 A | 5/1998 | Lindenmeier et al. |
| 5,765,418 A | 6/1998 | Rosenberg |
| 5,776,092 A | 7/1998 | Farin et al. |
| 5,788,688 A | 8/1998 | Bauer et al. |
| 5,797,907 A | 8/1998 | Clement |
| 5,800,431 A | 9/1998 | Brown |
| 5,836,897 A | 11/1998 | Sakurai et al. |
| 5,836,909 A | 11/1998 | Cosmescu |
| 5,836,944 A | 11/1998 | Cosmescu |
| D402,030 S | 12/1998 | Roberts et al. |
| D402,031 S | 12/1998 | Roberts et al. |
| 5,843,109 A | 12/1998 | Mehta et al. |
| 5,846,236 A | 12/1998 | Lindenmeier et al. |
| 5,859,527 A | 1/1999 | Cook |
| 5,868,768 A | 2/1999 | Wicherski et al. |
| 5,876,400 A | 3/1999 | Songer |
| 5,888,200 A | 3/1999 | Walen |
| 5,893,848 A | 4/1999 | Negus et al. |
| 5,893,849 A | 4/1999 | Weaver |
| 5,893,862 A | 4/1999 | Pratt et al. |
| 5,913,864 A | 6/1999 | Garito et al. |
| 5,919,219 A | 7/1999 | Knowlton |
| 5,928,159 A | 7/1999 | Eggers et al. |
| 5,938,589 A | 8/1999 | Wako et al. |
| 5,941,887 A | 8/1999 | Steen et al. |
| 5,944,737 A | 8/1999 | Tsonton et al. |
| 5,951,548 A | 9/1999 | DeSisto et al. |
| 5,951,581 A | 9/1999 | Saadat et al. |
| 5,954,686 A | 9/1999 | Garito et al. |
| 5,972,007 A | 10/1999 | Sheffield et al. |
| 6,004,318 A | 12/1999 | Garito et al. |
| 6,004,333 A | 12/1999 | Sheffield et al. |
| 6,004,335 A | 12/1999 | Vaitekunas et al. |
| 6,010,499 A | 1/2000 | Cobb |
| 6,022,347 A | 2/2000 | Lindenmeier et al. |
| 6,045,564 A | 4/2000 | Walen |
| 6,063,050 A | 5/2000 | Manna et al. |
| 6,068,603 A | 5/2000 | Suzuki |
| 6,068,627 A | 5/2000 | Orszulak et al. |
| 6,070,444 A | 6/2000 | Lontine et al. |
| 6,071,281 A | 6/2000 | Burnside et al. |
| 6,074,386 A | 6/2000 | Goble et al. |
| 6,074,387 A | 6/2000 | Heim et al. |
| 6,086,544 A | 7/2000 | Hibner et al. |
| 6,090,123 A | 7/2000 | Culp et al. |
| 6,099,525 A | 8/2000 | Cosmescu |
| 6,117,134 A | 9/2000 | Cunningham et al. |
| 6,139,547 A | 10/2000 | Lontine et al. |
| D433,752 S | 11/2000 | Saravia |
| 6,142,995 A | 11/2000 | Cosmescu |
| 6,146,353 A | 11/2000 | Platt, Jr. |
| 6,149,646 A * | 11/2000 | West et al. .............. 606/41 |
| 6,149,648 A | 11/2000 | Cosmescu |
| 6,156,035 A | 12/2000 | Songer |
| 6,197,024 B1 | 3/2001 | Sullivan |
| 6,200,311 B1 | 3/2001 | Danek et al. |
| D441,077 S | 4/2001 | Garito et al. |
| 6,213,999 B1 | 4/2001 | Platt, Jr. et al. |
| 6,214,003 B1 | 4/2001 | Morgan et al. |
| 6,231,591 B1 * | 5/2001 | Desai ............... 606/210 |
| 6,238,388 B1 | 5/2001 | Ellman et al. |
| 6,241,723 B1 | 6/2001 | Heim et al. |
| 6,241,753 B1 | 6/2001 | Knowlton |
| 6,249,706 B1 | 6/2001 | Sobota et al. |
| 6,251,110 B1 | 6/2001 | Wampler |
| 6,257,241 B1 | 7/2001 | Wampler |
| 6,258,088 B1 | 7/2001 | Tzonev et al. |
| 6,270,476 B1 * | 8/2001 | Santoianni et al. ........ 604/95.04 |
| 6,273,862 B1 | 8/2001 | Privitera et al. |
| 6,277,083 B1 | 8/2001 | Eggers et al. |
| 6,286,512 B1 | 9/2001 | Loeb et al. |
| 6,287,305 B1 | 9/2001 | Heim et al. |
| 6,287,344 B1 | 9/2001 | Wampler et al. |
| 6,312,441 B1 | 11/2001 | Deng |
| 6,325,799 B1 | 12/2001 | Goble |
| D453,222 S | 1/2002 | Garito et al. |
| D453,833 S | 2/2002 | Hess |
| 6,350,276 B1 | 2/2002 | Knowlton |
| 6,352,544 B1 | 3/2002 | Spitz |
| 6,355,034 B2 | 3/2002 | Cosmescu |
| 6,358,281 B1 | 3/2002 | Berrang et al. |
| 6,361,532 B1 | 3/2002 | Burek |
| D457,955 S | 5/2002 | Bilitz |
| 6,386,032 B1 | 5/2002 | Lemkin et al. |
| 6,395,001 B1 | 5/2002 | Ellman et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,725 B1 | 6/2002 | Khandkar et al. |
| 6,413,255 B1 | 7/2002 | Stern |
| 6,416,491 B1 | 7/2002 | Edwards et al. |
| 6,416,509 B1 | 7/2002 | Goble et al. |
| 6,425,912 B1 | 7/2002 | Knowlton |
| 6,458,122 B1 | 10/2002 | Pozzato |
| 6,458,125 B1 | 10/2002 | Cosmescu |
| 6,461,352 B2 | 10/2002 | Morgan et al. |
| 6,464,702 B2 | 10/2002 | Schulze et al. |
| 6,471,659 B2 | 10/2002 | Eggers et al. |
| 6,494,882 B1 | 12/2002 | Lebouitz et al. |
| 6,500,169 B1 | 12/2002 | Deng |
| 6,511,479 B2 | 1/2003 | Gentelia et al. |
| 6,526,320 B2 | 2/2003 | Mitchell |
| 6,551,313 B1 | 4/2003 | Levin |
| 6,558,383 B2 | 5/2003 | Cunningham et al. |
| 6,585,664 B2 | 7/2003 | Burdorff et al. |
| 6,589,239 B2 | 7/2003 | Khandkar et al. |
| 6,610,054 B1 | 8/2003 | Edwards et al. |
| 6,610,057 B1 | 8/2003 | Ellman et al. |
| 6,616,658 B2 | 9/2003 | Ineson |
| 6,618,626 B2 | 9/2003 | West, Jr. et al. |
| 6,620,161 B2 | 9/2003 | Schulze et al. |
| 6,632,193 B1 | 10/2003 | Davison et al. |
| 6,652,514 B2 | 11/2003 | Ellman et al. |
| 6,662,053 B2 | 12/2003 | Borkan |
| 6,669,691 B1 | 12/2003 | Taimisto |
| 6,685,701 B2 | 2/2004 | Orszulak et al. |
| 6,685,704 B2 | 2/2004 | Greep |
| 6,702,812 B2 | 3/2004 | Cosmescu |
| 6,710,546 B2 | 3/2004 | Crenshaw |
| 6,712,813 B2 | 3/2004 | Ellman et al. |
| 6,719,746 B2 | 4/2004 | Blanco |
| 6,740,079 B1 | 5/2004 | Eggers et al. |
| 6,747,218 B2 | 6/2004 | Huseman et al. |
| D493,530 S | 7/2004 | Reschke |
| D493,888 S | 8/2004 | Reschke |
| D494,270 S | 8/2004 | Reschke |
| D495,051 S | 8/2004 | Reschke |
| D495,052 S | 8/2004 | Reschke |
| 6,794,929 B2 | 9/2004 | Pelly |
| 6,830,569 B2 | 12/2004 | Thompson et al. |
| 6,840,948 B2 | 1/2005 | Albrecht et al. |
| 6,855,140 B2 | 2/2005 | Albrecht et al. |
| 6,902,536 B2 | 6/2005 | Manna et al. |
| 6,905,496 B1 | 6/2005 | Ellman et al. |
| 6,923,804 B2 | 8/2005 | Eggers et al. |
| 6,923,809 B2 | 8/2005 | Eggers et al. |
| 6,939,347 B2 | 9/2005 | Thompson |
| 6,955,674 B2 | 10/2005 | Eick et al. |
| D515,412 S | 2/2006 | Waaler et al. |
| 7,033,353 B2 | 4/2006 | Stoddard et al. |
| D521,641 S | 5/2006 | Reschke et al. |
| D535,396 S | 1/2007 | Reschke et al. |
| 7,156,842 B2 | 1/2007 | Sartor et al. |
| 7,156,844 B2 | 1/2007 | Reschke et al. |
| 7,169,143 B2 | 1/2007 | Eggers et al. |
| 7,235,072 B2 | 6/2007 | Sartor et al. |
| 7,241,294 B2 | 7/2007 | Reschke |
| 7,244,257 B2 | 7/2007 | Podhajsky et al. |

| | | |
|---|---|---|
| 7,311,706 B2 | 12/2007 | Schoenman et al. |
| 7,393,354 B2 | 7/2008 | Buchman, II et al. |
| 7,412,296 B2 * | 8/2008 | Yamaguchi et al. ............ 700/98 |
| 7,449,022 B2 * | 11/2008 | Quick et al. .................... 606/45 |
| 2001/0047183 A1 | 11/2001 | Privitera et al. |
| 2001/0049524 A1 | 12/2001 | Morgan et al. |
| 2002/0019596 A1 | 2/2002 | Eggers et al. |
| 2002/0019631 A1 | 2/2002 | Kidder et al. |
| 2002/0022838 A1 | 2/2002 | Cunningham et al. |
| 2002/0026145 A1 | 2/2002 | Bagaoisan et al. |
| 2002/0035364 A1 | 3/2002 | Schoenman et al. |
| 2002/0049427 A1 | 4/2002 | Wiener et al. |
| 2002/0058958 A1 | 5/2002 | Walen |
| 2002/0087179 A1 | 7/2002 | Culp et al. |
| 2002/0095199 A1 | 7/2002 | West, Jr. et al. |
| 2002/0103485 A1 | 8/2002 | Melnyk et al. |
| 2002/0111622 A1 | 8/2002 | Khandkar et al. |
| 2002/0133148 A1 | 9/2002 | Daniel et al. |
| 2002/0151886 A1 | 10/2002 | Wood |
| 2002/0151887 A1 | 10/2002 | Stern et al. |
| 2002/0156471 A1 | 10/2002 | Stern et al. |
| 2002/0173776 A1 | 11/2002 | Batchelor et al. |
| 2002/0198519 A1 | 12/2002 | Qin et al. |
| 2003/0004508 A1 | 1/2003 | Morgan et al. |
| 2003/0014043 A1 | 1/2003 | Henry et al. |
| 2003/0032950 A1 | 2/2003 | Altshuler et al. |
| 2003/0050633 A1 | 3/2003 | Ellman et al. |
| 2003/0055421 A1 | 3/2003 | West et al. |
| 2003/0061661 A1 | 4/2003 | Borders et al. |
| 2003/0065321 A1 | 4/2003 | Carmel et al. |
| 2003/0078572 A1 | 4/2003 | Pearson et al. |
| 2003/0083655 A1 | 5/2003 | Van Wyk |
| 2003/0088247 A1 | 5/2003 | Ineson |
| 2003/0109864 A1 | 6/2003 | Greep et al. |
| 2003/0109865 A1 | 6/2003 | Greep et al. |
| 2003/0130663 A1 | 7/2003 | Walen |
| 2003/0144680 A1 | 7/2003 | Kellogg et al. |
| 2003/0163125 A1 | 8/2003 | Greep |
| 2003/0199856 A1 | 10/2003 | Hill et al. |
| 2003/0199866 A1 | 10/2003 | Stern et al. |
| 2003/0199869 A1 | 10/2003 | Johnson et al. |
| 2003/0212393 A1 | 11/2003 | Knowlton et al. |
| 2003/0212397 A1 | 11/2003 | Avrahami et al. |
| 2003/0216728 A1 | 11/2003 | Stern et al. |
| 2003/0220635 A1 | 11/2003 | Knowlton et al. |
| 2003/0220638 A1 | 11/2003 | Metzger |
| 2003/0225401 A1 | 12/2003 | Eggers et al. |
| 2003/0229341 A1 | 12/2003 | Albrecht et al. |
| 2003/0229343 A1 | 12/2003 | Albrecht et al. |
| 2004/0000316 A1 | 1/2004 | Knowlton et al. |
| 2004/0002704 A1 | 1/2004 | Knowlton et al. |
| 2004/0002705 A1 | 1/2004 | Knowlton et al. |
| 2004/0010246 A1 | 1/2004 | Takahashi |
| 2004/0015160 A1 | 1/2004 | Lovewell |
| 2004/0015161 A1 | 1/2004 | Lovewell |
| 2004/0015162 A1 | 1/2004 | McGaffigan |
| 2004/0015216 A1 | 1/2004 | DeSisto |
| 2004/0024395 A1 | 2/2004 | Ellman et al. |
| 2004/0024396 A1 | 2/2004 | Eggers |
| 2004/0030328 A1 | 2/2004 | Eggers et al. |
| 2004/0030330 A1 | 2/2004 | Brassell et al. |
| 2004/0030332 A1 | 2/2004 | Knowlton et al. |
| 2004/0030367 A1 | 2/2004 | Yamaki et al. |
| 2004/0034346 A1 | 2/2004 | Stern et al. |
| 2004/0054370 A1 | 3/2004 | Given |
| 2004/0111087 A1 | 6/2004 | Stern et al. |
| 2004/0124964 A1 | 7/2004 | Wang et al. |
| 2004/0127889 A1 | 7/2004 | Zhang et al. |
| 2004/0143677 A1 | 7/2004 | Novak |
| 2004/0147909 A1 | 7/2004 | Johnston et al. |
| 2004/0162553 A1 | 8/2004 | Peng et al. |
| 2004/0167512 A1 | 8/2004 | Stoddard et al. |
| 2004/0172011 A1 | 9/2004 | Wang et al. |
| 2004/0172015 A1 | 9/2004 | Novak |
| 2004/0172016 A1 | 9/2004 | Bek et al. |
| 2004/0181140 A1 | 9/2004 | Falwell et al. |
| 2004/0243120 A1 | 12/2004 | Orszulak et al. |
| 2004/0267252 A1 | 12/2004 | Washington et al. |
| 2004/0267254 A1 | 12/2004 | Manzo et al. |
| 2004/0267297 A1 | 12/2004 | Malackowski |
| 2005/0033286 A1 | 2/2005 | Eggers et al. |
| 2005/0059858 A1 | 3/2005 | Frith et al. |
| 2005/0059967 A1 | 3/2005 | Breazeale, Jr. et al. |
| 2005/0065510 A1 | 3/2005 | Carmel et al. |
| 2005/0070891 A1 | 3/2005 | DeSisto |
| 2005/0085804 A1 | 4/2005 | McGaffigan |
| 2005/0096645 A1 | 5/2005 | Wellman et al. |
| 2005/0096646 A1 | 5/2005 | Wellman et al. |
| 2005/0096681 A1 | 5/2005 | Desinger et al. |
| 2005/0113817 A1 | 5/2005 | Isaacson et al. |
| 2005/0113818 A1 | 5/2005 | Sartor et al. |
| 2005/0113824 A1 | 5/2005 | Sartor et al. |
| 2005/0113825 A1 | 5/2005 | Cosmescu |
| 2005/0149001 A1 | 7/2005 | Uchikubo et al. |
| 2005/0154385 A1 | 7/2005 | Heim et al. |
| 2006/0041257 A1 | 2/2006 | Sartor et al. |
| 2006/0058783 A1 | 3/2006 | Buchman |
| 2006/0178667 A1 | 8/2006 | Sartor et al. |
| 2006/0241577 A1 * | 10/2006 | Balbierz et al. ................. 606/32 |
| 2007/0049926 A1 | 3/2007 | Sartor |
| 2007/0093810 A1 | 4/2007 | Sartor |
| 2007/0142832 A1 | 6/2007 | Sartor |
| 2007/0260239 A1 | 11/2007 | Podhajsky et al. |
| 2007/0260240 A1 | 11/2007 | Rusin |

FOREIGN PATENT DOCUMENTS

| | | |
|---|---|---|
| DE | 24 60 481 A1 | 6/1976 |
| DE | 30 45 996 | 7/1982 |
| EP | 0186369 A | 7/1986 |
| EP | 1050277 | 11/2000 |
| EP | 1050279 | 11/2000 |
| EP | 1082945 | 3/2001 |
| EP | 1293171 | 3/2003 |
| EP | 1 645 233 | 4/2006 |
| EP | 1645233 | 4/2006 |
| EP | 1645234 | 4/2006 |
| EP | 1656900 | 5/2006 |
| EP | 1852078 | 11/2007 |
| FR | 2235669 | 1/1975 |
| FR | 2798579 | 3/2001 |
| WO | WO 94/20032 | 9/1994 |
| WO | WO 96/39086 | 12/1996 |
| WO | WO 98/43264 | 10/1998 |
| WO | WO 01/64122 | 9/2001 |
| WO | WO 02/47568 A1 | 6/2002 |
| WO | WO 2004/010883 A1 | 2/2004 |
| WO | WO 2004/045436 A1 | 6/2004 |
| WO | WO 2004/073753 A2 | 9/2004 |
| WO | WO 2005/060849 A1 | 7/2005 |

OTHER PUBLICATIONS

International Search Report from PCT-US03-37111; Jul. 21, 2004.
International Search Report from PCT-US04-04685; Aug. 6, 2004.
International Search Report from EP-0401-5980; Sep. 30, 2004.
International Search Report from PCT-US03-22900; Nov. 20, 2003.
International Search Report from EP 05019882.9 dated Feb. 16, 2006.
International Search Report from EP 05021777.7 dated Feb. 23, 2006.
International Search Report from EP 06014461.5 dated Oct. 31, 2006.
International Search Report from EP 07009028 dated Jul. 16, 2007.
International Search Report from EP 06 00 5540 dated Sep. 24, 2007.
International Search Report from EP 08 00 2357 dated Jun. 30, 2008.
International Search Report from EP 06 00 6908 dated Feb. 25, 2009.
International Search Report from Application No. EP 06 00 6908 dated Feb. 25, 2009.
International Search Report from Application No. EP 08 02 1070 dated Apr. 1, 2009.
Zucker, Karl, Surgical Laparoscopy, Lippincott Williams & Wilkins, Ed. 2, 2001 (2 pages).

* cited by examiner

| B's Instrument Model / Type | A's Instrument Model / Type |||| 
|---|---|---|---|---|
| | i | ii | iii | iv |
| i | | | | |
| ii | | | | |
| iii | | | | |
| iv | | | | |

FIG. 14

EXTENSION CUTTING BLADE

BACKGROUND

1. Technical Field

The present disclosure relates generally to a device, a system, and a method of electrosurgery and, more particularly, to a method and device adapted for single incision laparoscopic surgery (SILS) to maximize the manipulability of electrosurgical instruments used during a SILS procedure.

2. Background

Two popular electrosurgical techniques are monopolar electrosurgery and bipolar electrosurgery. Monopolar electrosurgical techniques deliver alternating current electrosurgical energy from an exposed or an active electrode, through the patient's body, to a return pad or an electrode which is externally attached to a suitable location on the patient's skin. Bipolar electrosurgical methods deliver electrosurgical energy from a first exposed electrode in which both the first and the second electrodes are typically disposed within the patient's body, for example, the opposing jaws of electrosurgical forceps.

Electrosurgical instruments are devices that deliver radiofrequency (RF) energy to a tissue site, such as an electrosurgical instrument. The term "electrosurgical instrument," as used herein, is intended to include instruments having a hand-piece attached to an active electrode and used to cauterize, coagulate, and/or cut tissue. Typically, the electrosurgical instrument may be operated by a hand-switch or a foot switch, and are hand-held.

The waveforms produced by the RF source may yield a predetermined electrosurgical effect such as electrosurgical cutting, blending, or coagulation. Coagulation is defined as a process of desiccating tissue, wherein the tissue cells are ruptured and dehydrated. Electrosurgical cutting and dissecting include the application of electrosurgical energy to tissue to produce a cutting, dissecting, and/or dividing effect. Blending includes the function of cutting (dissecting) with the production of a hemostasis effect. Hemostasis is defined as the process of liquefying tissue collagen so that it becomes a fused mass.

The active electrode is an electrically conducting element, which is usually enlongated and may be in the form of a thin blade with a pointed or rounded distal end. Alternatively, the active electrode can include an enlongated narrow cylindrical needle that is either solid or hollow with a flat, rounded, pointed, or slanted distal end. The hand-piece of the electrosurgical instrument is connected to a suitable electrosurgical energy source (generator) that produces the RF energy needed for the operation of the electrosurgical instrument. In general, when performing an operation with an electrosurgical instrument, electrical energy from the electrosurgical generator is conducted through the active electrode to the tissue at the site of the operation and then through the patient to a return electrode. The return electrode is selectively placed on the patient's body and attached to the generator by a conductive material.

One technique for electrosurgery, called single incision laparoscopic surgery (SILS), reduces scanning and accelerates healing. The SILS technique involves making one single small incision, instead of several, through which a surgeon operates. Typically, the surgery is performed around the umbilicus (belly button) area. Fewer incisions result in a faster recovery with less pain.

Within the single incision, typically three or four ports are placed for the insertion of electrosurgical instruments to the operative field. Usually, two or three ports are used for devices having a 5 mm diameter and at least one larger port having a 10 to 12 mm diameter to allow for the insertion of an endoscope. Since all the channels are parallel to one another within a single incision, the instrument handles often line up and interfere with each other. This problem may be offset somewhat by making a larger incision in the patient with the resultant delay in healing and increased scarring.

SUMMARY

The present disclosure is directed to a device, a system, and a method for electrosurgery, e.g., single incision laparoscopic surgery (SILS), to permit a surgeon to more easily use multiple electrosurgical instruments within a single access point, e.g., an incision, while minimizing interference between the instruments. In particular, multiple embodiments of shafts for electrosurgical instruments and electrosurgical methods adapted for this purpose are disclosed.

Disclosed herein is an electrosurgical instrument including a housing having a selectively contourable shaft that extends therefrom and at least one electrode disposed at a distal end of the shaft adapted to connect to all electrosurgical generator, wherein the shaft is selectively contourable to maximize the manipulability of the shaft when used with other instruments during a single incision laparoscopic surgery.

The shaft may be selectively contour able to form a contour selected from the group consisting of generally S shaped shafts, generally U shaped shafts, generally W shaped shafts, and generally sinusoidal shaped shafts.

The shaft may be selectively contourable to form two generally right angles defined therein.

The shaft may be made from a shape memory material.

The shaft may include a series of joints.

The shaft may include a helical coil.

A handle may be coupled to the shaft at a proximal end thereof, the handle being movable relative to the shaft.

The shaft may be sufficiently rigid to resist application of ordinary forces and torques applied during an electrosurgical procedure.

Also disclosed is a method of adjusting a contour of a shaft of an electrosurgical instrument to maximize manipulability of the instrument when used for an electrosurgical procedure, including the steps of: determining values for variables including instrument type, instrument number, number of instruments, and diameter of instrument shafts; inputting the values of the variables into a database, selecting an appropriate contour from the database's recommended contours; and adjusting the contour of the shaft to correspond with one of the recommended contours.

The method may further include the step of using a template to adjust the contour of the shaft. The template may include a contour displayed on a surface. The template may include a surface having a plurality of apertures configured as a grid adapted for the reception of pegs, wherein the pegs are adapted for the reception of an electrosurgical instrument shaft. The template may include a surface adapted for receiving a shaft of an electrosurgical instrument and a series of apertures adapted to receive screws along a non-parallel surface thereof for applying pressure to the shaft along predetermined points.

The database may include a list of preferred shapes for an electrosurgical shaft corresponding to a permutation of variables selected from the group consisting of instrument type, instrument model, shaft diameter, number of instruments, location of incision, size of incision, and physical characteristics of a user.

Also disclosed is an electrosurgical system including an electrosurgical generator adapted to connect to an electrosurgical instrument, the electrosurgical instrument having a contourable shaft including a distal end and a proximal end, and at least one electrode located proximate the distal end of the shaft, wherein the shaft is selectively contourable to maximize the manipulability of the shaft when used with other instruments during a single laparoscopic surgery.

BRIEF DESCRIPTION OF THE DRAWINGS

By way of description only, embodiments of the disclosure are described with reference to the accompanying drawings in which.

DETAILED DESCRIPTION

Particular embodiments of the present disclosure will be described herein with reference to the accompanying drawings. As shown in the drawings and as described throughout the following description, and as is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

Figure 1:
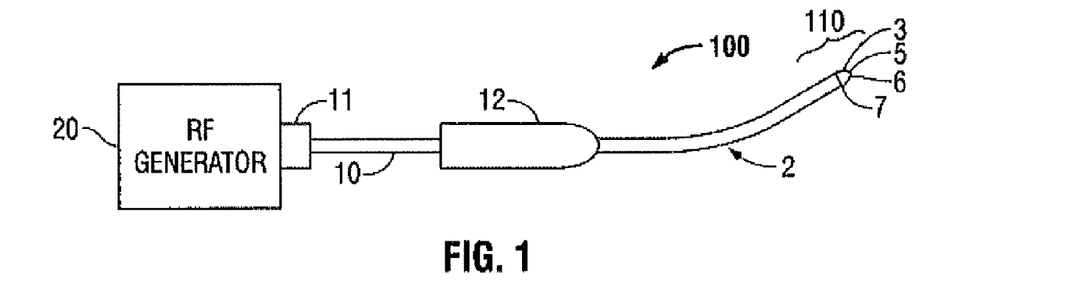
FIG. 1 is a schematic view of an electrosurgical system in accordance with the present disclosure.

As seen in FIG. 1, an electrosurgical system is disclosed having an RF generator 20 coupled to an electrosurgical instrument 100 including a handle 12 and a shaft 2 configured and adapted to support electrodes, e.g., electrodes 3, 5, and 6, at a distal end of the shaft 2 and the appropriate electrical connections, e.g., cable 10, for coupling one or more active electrodes and one return electrodes to a high frequency power supply, e.g., electrosurgical generator 20.

In embodiments, an end effector may be, but is not limited to, a cutting device, forceps, or a suction coagulator As shown in FIG. 1, an end effector 110 may include one or more active electrodes 3, 5, and 6. The electrodes 3, 5, and 6 may be supported within or near an insulating support 7 positioned at or near the distal end of the shaft 2. Electrodes 3, 5, and 6 are operably coupled to an electrosurgical generator 20 that is configured to supply radio frequency (RF) voltage, RF electronic current, or electrosurgical energy therein. By way of example only, electrosurgical generator 20 may be any one of the following, or equivalents thereof: the "FORCE FX®", "FORCE 2™", "FORCE 4™", "LIGASURE®", "FORCE EZ®", "FORCE 1C™", "SURGISTAT®", "SURGISTAT II™", generators manufactured by Valleylab, a division of Covidien, located in Boulder, Colo. It is contemplated that electrosurgical generator 14 can be preset to selectively provide an appropriate first predetermined RF signal (e.g., about 1 to 300 watts) for tissue cutting and an appropriate second predetermined RF signal (e.g., about 1 to 120 watts) for tissue coagulation. One such system is described in commonly-owned U.S. Pat. No. 6,033,399 entitled "ELECTROSURGICAL GENERATOR WITH ADAPTIVE POWER CONTROL" the entire contents of which are hereby incorporated by reference herein. Other systems have been described in commonly-owned U.S. Pat. No. 6,187,003 entitled "BIPOLAR ELECTROSURGICAL INSTRUMENT FOR SEALING VESSELS" the entire contents of which are also incorporated by reference herein.

In an embodiment, the generator may include a switch (not shown) to deliver either RF-current suitable for cutting or RF-current suitable for coagulation by applying, for example, suitable RF voltage to either the coagulation electrode pair 3 and 6 or the cutting electrode pair 5 and 6. The switch may be on the instrument or may be a handswitch or a footswitch.

Figure 2:
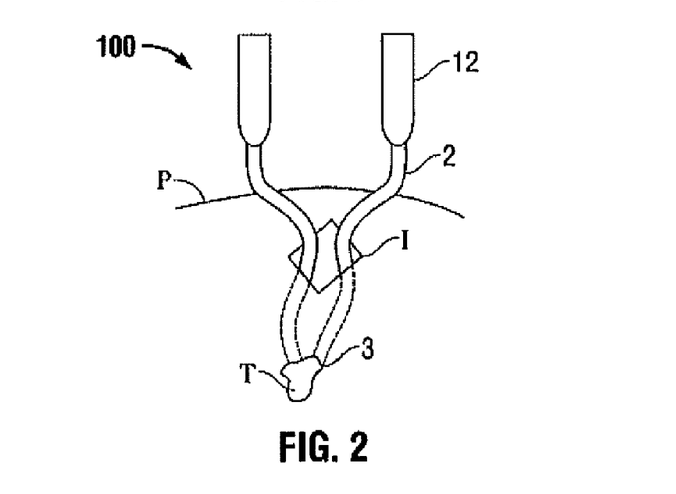
FIG. 2 is a schematic view of a cutting device in accordance with the present disclosure, engaged with a target lumen.

As shown in FIG. 2, the cutting device 100 may be inserted into a single incision I within a patient P to reach a target lumen T, for example, the gallbladder. As seen, the shaft 2 is bent so that the handle 12 is less likely to interact with other instruments and also creates more of a workspace for the surgeon. Such a configuration permits the distal end 3 of the shaft 2 to be much closer to one another than would otherwise be permitted, for example, thereby creating space for the surgeon's hands (not shown) without requiring the surgeon to hold the instruments further apart.

Figure 3:
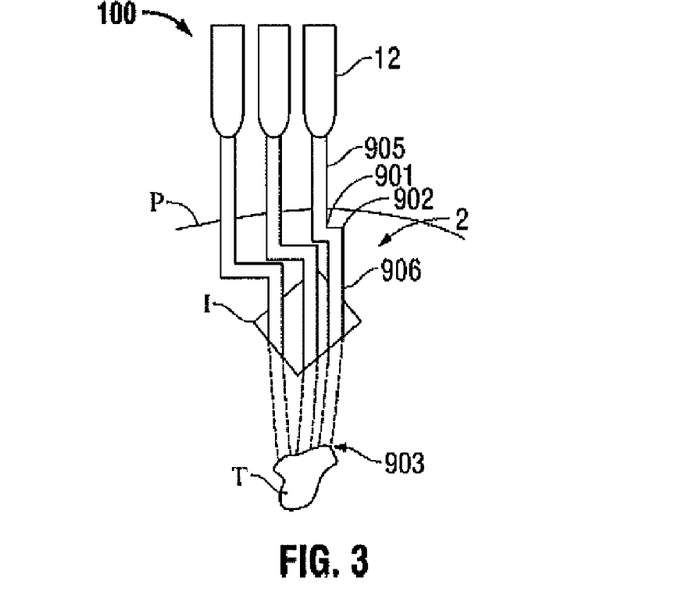
FIG. 3 is a schematic view of a cutting device in accordance with the present disclosure, engaged with a target lumen.

In an embodiment, as shown in FIG. 3, each cutting device 100 has a shaft 2 that forms two generally right angles 901 and 902. It is envisioned that by staggering the lengths of portions of the shaft 904, e.g. upper portion 905 and lower portion 906 that the shafts 900 may be spaced closely to one another in a parallel configuration while allowing for a full range of motion without interference from each shaft 2. Joints may be located at points 901 and 902 along the shaft 904, allowing the handle 12 to tilt with respect to the shaft 2. In still a further embodiment, handle 12 is capable of telescopic motion. The distal end 903 of the shaft 2 may include electrodes.

Figure 12:
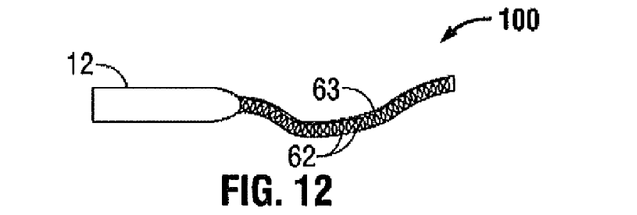
FIG. 12 is a schematic view of a cutting device having a helical coil in accordance with the present disclosure.
Figure 13:
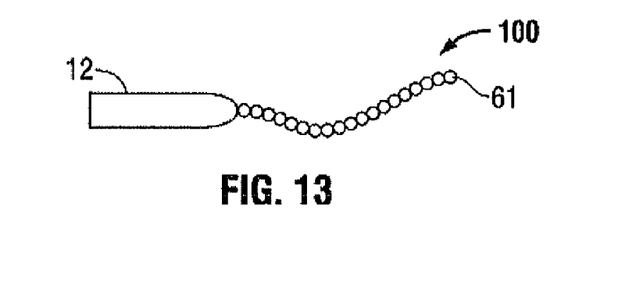
FIG. 13 is a schematic view of a cutting device having a series of joints in accordance with the present disclosure.

The shape of the shaft can be made to be adjustable in several ways, including, but not limited to the shaft being made of a shape memory material, comprising a series of joints, as shown in FIG. 12, and/or comprising a helical coil, as shown in FIG. 13. Once positioned as desired by the user, the shaft 2 in both of these embodiments may be locked in place for instance by a drawstring (not shown).

The shaft may be made of a material sufficiently rigid to resist the application of ordinary forces and torques applied to the device during an electrosurgical procedure. For instance, in one embodiment, the shaft 2 is made from any bendable material, including a shape memory alloy, including but not limited to AgCd, AuCd, CuAlNi, CuSn, CuZnSi, CuZnAl, CuZnSn, FePt, MnCu, FeMnSi, Pt alloys, CoNiAl, CoNiGa, TiPd, NiTi, and CuAlNi. Shape memory allows have the ability to be bent into a variety of shapes and will hold that shape until heated above a transition temperature, whereupon they will revert back to the original shape.

Alternatively, a series of joints and/or a helical coil may comprise the shaft 2 of the cutting device 100. The shaft 2 may be locked in place once the shaft's desired shape is achieved.

A method of preparing electrosurgical instrumentation for insertion into an incision within a patient, e.g., for use in single incision laparoscopic surgeries (SILS), includes the steps of providing a template displaying a shape corresponding to a desired shape for a shaft of an electrosurgical device and bending the shaft of the electrosurgical device in conformance with the shape determined by the template.

Figure 14:
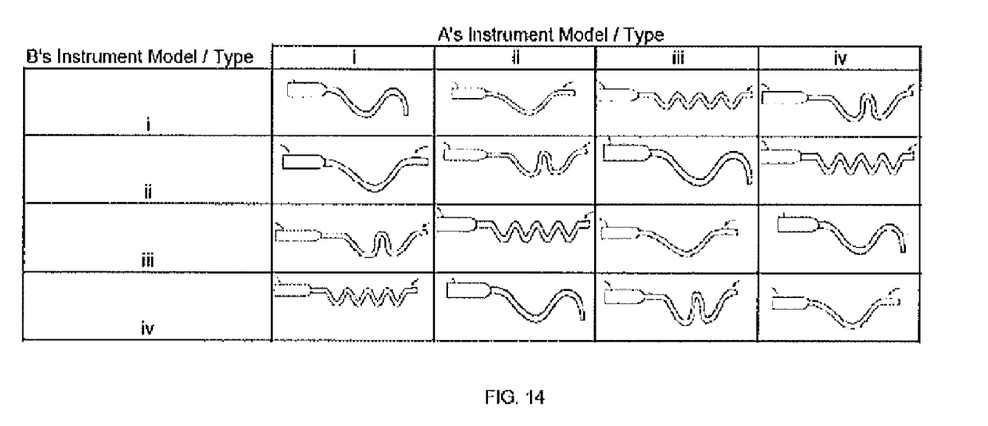
FIG. 14 is a schematic view of a database for selecting a contoured shaft for an electrosurgical instrument.

A database of recommended shaft configurations determined by a permutation of variables including, but not limited to, type or model number of an instrument, shaft diameter, location and size of an incision, the number of instruments to be inserted into the incision, and the physical characteristics of the user such as the size of the user's hands. As seen in FIG. 14, a surgeon may for example use a database to select an appropriate shaft configuration given the model and type numbers of instruments to be used.

Figure 4:
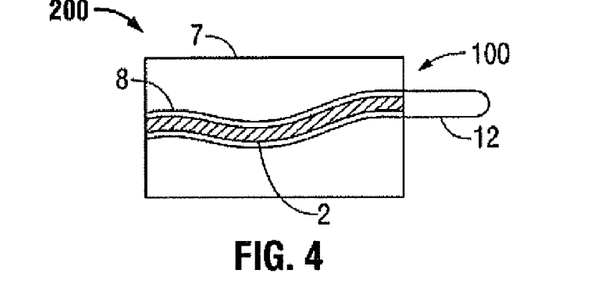
FIG. 4 is a schematic view of a template for shaping a shaft of a cutting device in accordance with the present disclosure.
Figure 5:
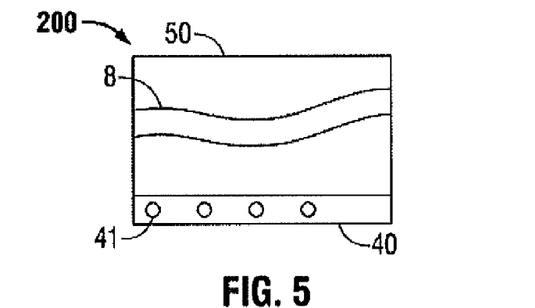
FIG. 5 is a schematic view of a template for shaping a shaft of a cutting device in accordance with the present disclosure.

In a further embodiment, a surgeon may quickly and easily determine the curvature necessitated by a particular procedure by using a template, as shown in FIGS. 4-7. As shown in FIG. 4, a template 200 is shown having a surface 7 including a curve 8. The electrosurgical cutting device 100 may be placed on the template 200 and the shaft 2 may be manipulated to conform with the curve 8 displayed on the surface 7. The curve 8 may also be displayed visually as shown in FIG. 5. In the embodiment shown in FIG. 5, a visual display 50 is coupled to a computer 40. A surgeon may enter variables into the computer 40 through controls 41, including such variables as shaft diameter, location of the target lumen, incision size, and the number of instruments to be used. Once entered, the curve 8 is shown on display 8 and the surgeon may use the displayed image to conform the shaft 2 to the displayed curve.

Figure 6:
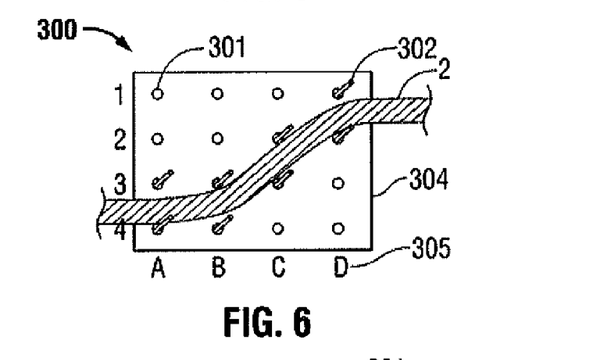
FIG. 6 is a schematic view of a template for shaping a shaft of a cutting device in accordance with the present disclosure.

Alternatively, a template 300 may include a surface including a plurality of holes 301 corresponding to a grid 305 adapted for the insertion of push pins 302, as shown in FIG. 6. A user, e.g., a surgeon, may enter variables for a given procedure, including instrument type and model number, number of instruments, shaft diameter, etc., and utilize a database to select a curve corresponding to that specific permutation. The database will then specify the appropriate locations for push pins 302 to be inserted into the holes 301.

Once the push pins 302 are inserted into the holes 301 within the surface 304 of the template 300 as specified in a database detailing the placement of the push pins 302 along the grid 305, a user may fit the shaft 2 between the push pins 302 until the shaft 2 conforms to the desired configuration for the particular procedure.

Figure 7:
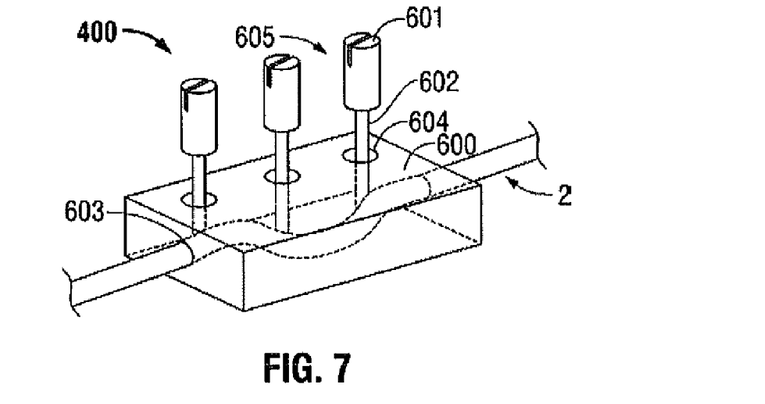
FIG. 7 is a schematic view of a template for shaping a shaft of a cutting device in accordance with the present disclosure.

In an embodiment, a template 400 for adjusting the shape of an electrosurgical device shaft including a box 600 having an opening 603 along one face of the box 600 and a series of screws 605 along another face of the box that is not parallel to the face having the opening 605. A marked thread 602 can be used to indicate the depth of the screw. In an embodiment, a database can indicate the desired depth of each screw 605 to achieve a desired shaft 2 contour upon the insertion of shaft 2. It is envisioned that one skilled in the art may make obvious substitutions for certain elements disclosed herein. For example, without limitation, it should be understood that the term "screw" connotes any device capable of maintaining a fixed position once inserted into a hole.

Figure 8:
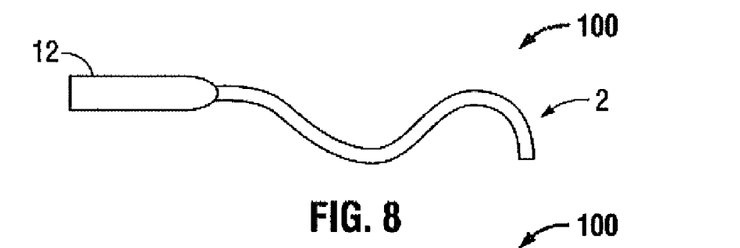
FIG. 8 is a schematic view of an embodiment of a contoured shaft in accordance with the present disclosure.
Figure 9:
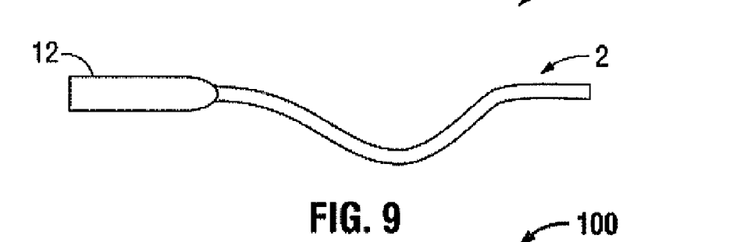
FIG. 9 is a schematic view of another contoured shaft in accordance with the present disclosure.
Figure 10:
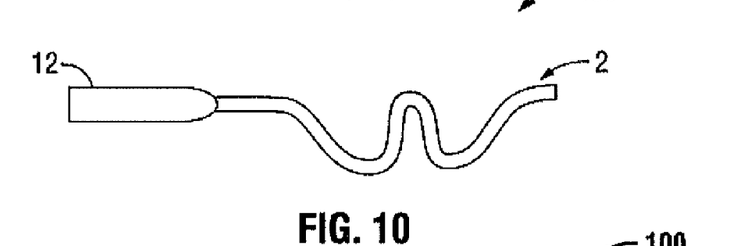
FIG. 10 is a schematic view of yet another contoured shaft in accordance with the present disclosure.
Figure 11:
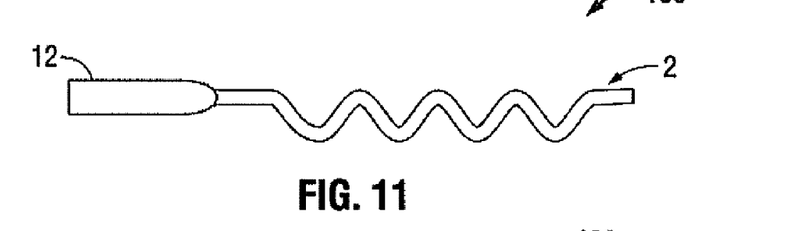
FIG. 11 is a schematic view of still another contoured shaft in accordance with the present disclosure.

Exemplary shapes of the shafts of the electrosurgical devices include a shaft having the shape of two substantially inversely symmetrical L's (FIG. 3), a generally S-shaped configuration (FIG. 8), a generally U-shaped configuration (FIG. 9), a generally W-shaped configuration (FIG. 10), a generally sinusoidal shaped configuration (FIG. 11).

It is envisioned that the present disclosure will permit a surgeon to more easily manipulate multiple instruments within a single access point. In particular, a greater range of manipulability is achieved by selecting electrosurgical instruments having shaft configurations purposefully designed to reduce the likelihood that the shafts will impede each shaft's range of motion.

What is claimed is:

1. An electrosurgical system, comprising:
   an electrosurgical generator;
   an electrosurgical instrument adapted to operably couple to the electrosurgical generator and having a contourable shaft including a distal end and a proximal end;
   at least one electrode located proximate the distal end of the shaft, wherein the shaft is selectively contourable to maximize the manipulability of the shaft when used with other instruments during a single laparoscopic surgery; and
   a database of shaft configurations determined by a permutation of variables.

2. The electrosurgical system in accordance with claim 1, wherein the variables are selected from the group consisting of an instrument, a shaft diameter, a location of an incision, a size of an incision, a number of instruments to be inserted into an incision, and a user's hand size.

3. The electrosurgical system in accordance with claim 1, further comprising a template having a curve representative of a shaft configuration displayed thereon.

4. The electrosurgical system in accordance with claim 1, further comprising a template including a surface having a plurality of apertures configured as a grid adapted for the reception of at least one peg, wherein the at least one peg is adapted to receive an electrosurgical instrument shaft.

5. The electrosurgical system in accordance with claim 4, wherein the placement of pegs is determined by the database of shaft configurations.

6. The electrosurgical system in accordance with claim 1, further comprising a template adapted to adjust the shape of the shaft, the template comprising:
   a first surface and a second surface, wherein the first surface is not parallel to the second surface;
   an opening defined in the first surface configured to receive the shaft;
   an aperture defined in the second surface configured to receive a screw for applying pressure to the shaft at a predetermined point.

7. The electrosurgical system in accordance with claim 6, further comprising a screw configured to operably engage the aperture having a marking on a thread thereof to indicate the depth of the screw within the aperture.

8. The electrosurgical system in accordance with claim 6, wherein the database includes a screw depth.

9. The electrosurgical system in accordance with claim 1, wherein the shaft is selectively contourable to form a contour selected from the group consisting of generally S shaped shafts, generally U shaped shafts, generally W shaped shafts, and generally sinusoidal shaped shafts.

10. The electrosurgical system in accordance with claim 1, wherein the shaft is selectively contourable to form two generally right angles defined therein.

11. The electrosurgical system in accordance with claim 1, wherein the shaft is made from a shape memory material.

12. The electrosurgical system in accordance with claim 1, wherein the shaft includes a series of joints.

13. The electrosurgical system in accordance with claim 1, wherein the shaft includes a helical coil.

14. The electrosurgical system in accordance with claim 1, wherein a handle is coupled to the shaft at a proximal end thereof, the handle being movable relative to the shaft.

15. The electrosurgical system in accordance with claim 1, wherein the shaft is sufficiently rigid to resist application of ordinary forces and torques applied during an electrosurgical procedure.

16. A method of adjusting a contour of a shaft of an electrosurgical instrument to maximize manipulability of the instrument when used for an electrosurgical procedure, comprising the steps of:
   determining values for variables including instrument type, instrument number, number of instruments, and diameter of instrument shafts;
   inputting the values of the variables into a database;
   selecting an appropriate contour from the database's recommended contours; and
   adjusting the contour of the shaft to correspond with one of the recommended contours.

17. The method of claim 16 further comprising the step of: using a template to adjust the contour of the shaft.

18. The method of claim 17 wherein the template includes a contour displayed on a surface.

19. The method of claim 17 wherein the template includes:
   a surface having a plurality of apertures configured as a grid adapted for the reception of pegs, wherein the pegs are adapted for the reception of an electrosurgical instrument shaft.

20. The method of claim 17 wherein the template includes:
   a surface adapted for receiving a shaft of an electrosurgical instrument; and
   a series of apertures adapted to receive screws along a non-parallel surface thereof for applying pressure to the shaft along predetermined points.

21. The method of claim 16 wherein the database includes:
   a list of preferred shapes for an electrosurgical shaft corresponding to a permutation of variables selected from the group consisting of instrument type, instrument model, shaft diameter, number of instruments, location of incision, size of incision, and physical characteristics of a user.

\* \* \* \* \*